United States Patent [19]

Jacquet et al.

[11] 4,233,430
[45] Nov. 11, 1980

[54] ANTI-SOLAR ACRYLAMIDE DERIVATIVE POLYMERS, METHOD OF MAKING THE SAME AND COSMETIC COMPOSITIONS CONTAINING THE SAME

[75] Inventors: Bernard Jacquet, Antony; Christos Papantoniou, Epinay-sur-Seine; Pierre Dufaure; Claude Mahieu, both of Paris, all of France

[73] Assignee: L'Oreal, Paris, France

[21] Appl. No.: 35,009

[22] Filed: May 1, 1979

Related U.S. Application Data

[60] Division of Ser. No. 715,565, Aug. 18, 1976, which is a continuation-in-part of Ser. No. 374,058, Jun. 27, 1973, Pat. No. 3,980,617.

[30] Foreign Application Priority Data

Jun. 26, 1973 [FR] France .................. 73 23254
Jul. 29, 1976 [FR] France .................. 76 23174

[51] Int. Cl.$^2$ .......................... A61K 7/44; A61K 7/42
[52] U.S. Cl. ........................ 526/259; 526/260; 526/261; 526/303; 526/304; 526/307; 424/59; 424/60
[58] Field of Search ............... 526/303, 304, 307, 256, 526/258, 260, 259, 261

[56] References Cited

U.S. PATENT DOCUMENTS

| 3,627,831 | 12/1971 | Emden et al. .......... 526/313 |
| 3,980,617 | 9/1976 | Jacquet et al. .......... 424/59 |

FOREIGN PATENT DOCUMENTS

1407670  9/1975  United Kingdom ............ 526/304

OTHER PUBLICATIONS

Chem. Abstracts, vol. 89, entry 6867x.
Chem. Abstracts, vol. 88, entry 191776x.

*Primary Examiner*—Joseph L. Schofer
*Assistant Examiner*—Peter F. Kulkosky
*Attorney, Agent, or Firm*—Cushman, Darby & Cushman

[57] ABSTRACT

An anti-solar polymer has in the macromolecular chain thereof at least one unit of the formula

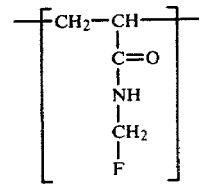

wherein F is a residue derived from an aromatic compound.

The anti-solar polymer can also be one having in the macromolecular chain thereof at least one unit of the formula

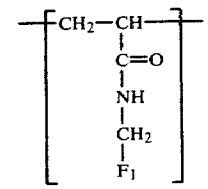

wherein $F_1$ is

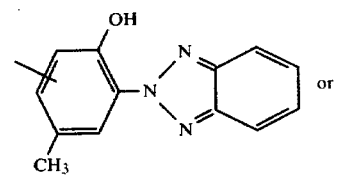

or

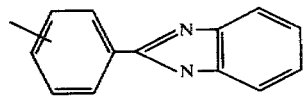

These polymers have the ability to absorb wave lengths of light in the range of about 280–315 millimicrons. The polymers are employed in a cosmetic composition.

11 Claims, No Drawings

ANTI-SOLAR ACRYLAMIDE DERIVATIVE POLYMERS, METHOD OF MAKING THE SAME AND COSMETIC COMPOSITIONS CONTAINING THE SAME

This application is a division of our application, Ser. No. 715,565, filed Aug. 18, 1976 which, in turn, is a continuation-in-part of our application, Ser. No. 374,058, filed June 27, 1973, now U.S. Pat. No. 3,980,617.

The present invention relates to novel "anti-solar" polymers which are particularly useful in cosmetic preparations, to the process for preparing these new polymers and to cosmetic compositions containing the same.

Sunburn, or erythema, results from the excessive exposure of human skin to the rays of the sun and the wave lengths of light in the range of 280 to 315 millimicrons, often called the "erythematous zone" are those which produce such sunburn.

Below this wave length range the sun rays do not present any particular danger, for they are filtered by the ozone in the atmosphere.

However, the UV rays which are responsible for or which produce a desirable suntan are those in the zone ranging from 315 to 400 millimicrons.

Consequently, if one desires to be exposed to solar radiation, it is important that the skin be protected with the aid of a composition containing a substance which absorbs the UV rays in the erythematous zone, thereby avoiding an undesirable sunburn, which composition however also transmits those wave lengths in the range of 315 to 400 millimicrons so as to obtain a desirable suntan.

Heretofore a number of formulations have been proposed for this purpose. For the most part, they are based on aromatic compounds exhibiting an absorption in the UV in the zone between 280 and 315 millimicrons and, more particularly, between 295 and 305 millimicrons.

In addition to this absorbing power, such compounds must have other properties and in particular they must not absorb the wave lengths of light in the zone ranging from 315 to 400 millimicrons, they should be non-volatile and they should also be resistant to both fresh and salt water and to perspiration. Additionally they should exhibit cosmetic compatibility with other components which may be present in suntan formulations and they should be non-odorous, non-toxic and non-irritating, i.e. entirely harmless to the user.

Among these characteristics, non-toxicity and dermotological compatibility are of great importance.

Representative aromatic compounds which have heretofore been employed in suntan preparations include derivatives of para-aminobenzoic acid, derivatives of anthranilic acid, derivatives of cinnamic acid and dihydroxy and trihydroxy cinnamic acid, derivatives of coumarin and the like.

The rather current widespread use of such compounds as an "anti-solar filter", is not without certain disadvantages. Certain of these substances do not exhibit sufficient efficiency in their ability to absorb the wave lengths of light in the erythematous zone. Moreover many do not possess the requisite solubility characteristics necessary so as to be utilized in many different types of formulation, and finally, because of their low molecular weight, many are able to penetrate through the epidermis of the skin into the human body which, in certain cases, can cause unfavorable side effects.

In an effort to remedy the inconveniences of these compounds, it has also been proposed to fix on macromolecular chains of certain copolymers, filters absorbing in UV in the erythematous region.

Among the polymers of this type described in the literature, one can in particular cite those resulting from the polymerization of 2-hydroxy (3-acryloxy or methacryloxy-2hydroxy-4-propoxy) benzophenone with a comonomer of the methyl methacrylate type or of an unsaturated carboxylic acid such as acrylic, methacrylic, itaconic or crotonic acid, or the like.

However, these copolymers have not been found to be fully effective in cosmetic compositions because often they are quite difficult to formulate with other components generally found in a wide variety of antisolar compositions and often they absorb only a portion of the undesirable wave lengths in the erythematous zone.

In effect, the nature of the function which permits the linking of the filter moiety to the polymeric chain of these known materials seriously limits the number of aromatic residues which impart the filtering or absorping characteristics to the polymer and thus it has been found that there is often not a sufficient amount of such aromatic residues to provide the degree of efficacy desired or required.

To overcome these disadvantages, the applicants have not provided anti-solar polymers wherein the residue which imparts to the polymer the ability to absorb wave lengths in the erythematous zone is linked to the polymeric chain by an intermediate chemical function of a particular type.

Thus in a first embodiment, the present invention relates to an anti-solar polymer which contains in the macromolecular chain thereof at least one unit having the formula

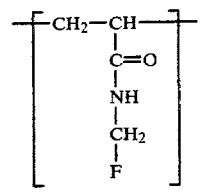

I wherein F is a residue derived from an aromatic compound imparting to the polymer the ability to absorb those wave lengths of light in the range of about 280 to 315 millimicrons.

In a second embodiment of the present invention the anti-solar polymer contains in the macromolecular chain thereof at least one unit having the formula

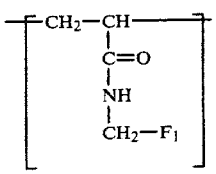

II wherein $F_1$ represents a member selected from the group consisting of:

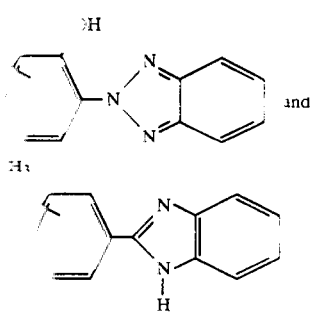

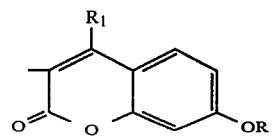

The new polymers according to this embodiment of the invention are preferably copolymers (bi-polymers, terpolymers, etc.). That is to say, that they carry both the units of formula II and one or more other units derived from ethylenically unsaturated monomers.

The ethylenically unsaturated monomers or comonomers able to enter into the production of the copolymers according to the invention are selected as a function of the type of formulation that one desires to produce.

It has been observed that the use of the anti-solar polymers of the present invention in cosmetic compositions is highly advantageous since the linking of the F or $F_1$ residue to the macromolecular chain avoids or at least significantly retards the migration of an otherwise non-linked absorbent moiety through the skin into the human body thereby avoiding any undesirable side effects which have been experienced in the use of heretofore known anti-solar filters.

The importance of this feature can be easily appreciated especially since repeated applications of the anti-solar compositions of this invention are generally not necessary to achieve the desired results which thereby avoids any substantial risk of a massive absorption of the filter compounds into the body.

The anti-solar polymers of this invention generally have an average molecular weight generally between 2,000 and 1,000,000.

The radical in formula I above, represented by F, can be derived from a variety of aromatic compounds. Representative radicals include aryl, alkyl aryl, alkenylaryl, each of which can optionally be substituted, as well as aromatic heterocyclic radicals, also optionally substituted.

In particular the radical F can be selected from the group consisting of:

1)

2)

3)

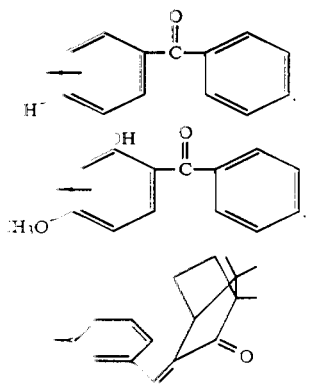

-continued

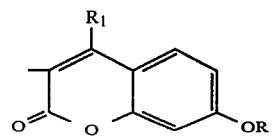

wherein R is selected from the hydrogen and $CH_3$ and $R_1$ is selected from the group consisting of $CH_3$ and $OCH_3$.

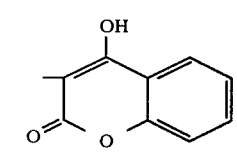

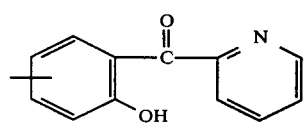

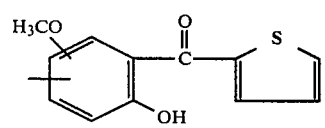

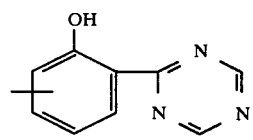

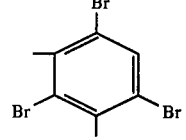

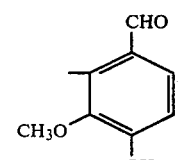

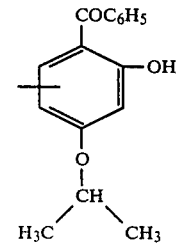

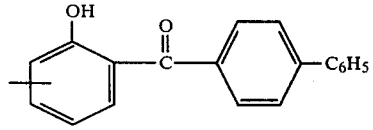

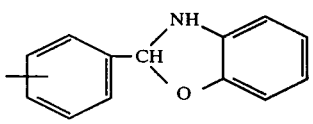

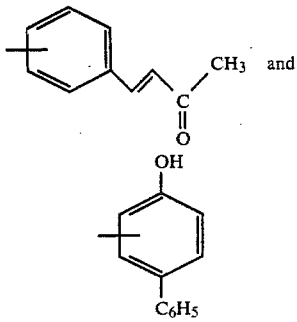

(14)

(15)

Because of the variety of the nature of the radicals F and $F_1$ that can be linked to the polymer chain, it is possible to fully cover the erythematous zone simply by a judicious selection of the appropriate compounds to be linked to said polymer chain.

The anti-solar polymers of the present invention can be either homopolymers, copolymers, terpolymers and the like.

Thus, in the homopolymers of this invention, in the repeating unit defined by formulas I and II the values of F and $F_1$ are the same whereas in a group of copolymers of this invention, in the said repeating unit, the values of F and/or $F_1$ can be different.

The ability to obtain copolymers having fixed on their macromolecular chains F and/or $F_1$ radicals of differing structures is a highly desirable feature since by choosing the appropriate compounds, it is thus possible to provide a single copolymer which can cover the entire erythematous zone, thereby producing an anti-solar filter of great efficacy.

The polymers of the invention can also be bipolymers, terpolymers or the like, and they can include, at the same time, (1) units of formula I or II wherein F or $F_1$ is the same and one or more other units can be derived from ethylenically unsaturated monomers, or (2) units of formula I or II containing F and/or $F_1$ radicals which are different, and one or more other units can be derived from ethylenically unsaturated monomers.

The selection of the ethylenically unsaturated monomers or comonomers for use in the production of the polymers of the present invention is generally dependent on the function of the desired use of the resulting composition or, more exactly, on the type of formulation that is desired.

Thus is is possible to impart to the anti-solar polymers of this invention different characteristics by varying the nature of the comonomer used.

Representative comonomers include:
(a) N-vinylpyrrolidone,
(b) N-methacryloyl D-glucosamine,
(c) dimethylaminoethyl methacrylate
(d) stearyl methacrylate
(e) stearyl acrylate and
(f) methyl methacrylate The first three of these comonomers generally increase the solubility of the resulting polymer in aqueous solutions while the last three ordinarily increase the solubility of the polymer in oil.

In another embodiment of the present invention the copolymers can have the formula

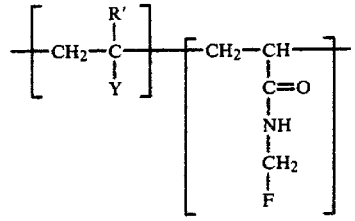

wherein
F has the meaning given above,
R' represents hydrogen or methyl and
Y represents a radical selected from the group consisting of

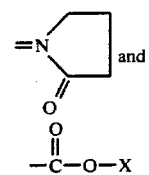

(i)

(ii)

wherein X represents D-glucosamine, dimethylamino ethyl optionally quaternized and $C_{18}H_{37}$.

In yet another embodiment of the present invention, the copolymers can have the formula:

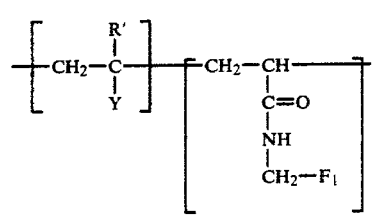

IV wherein
$F_1$ has the same meaning above,
R' represents hydrogen or methyl and
Y represents a member selected from the group consisting of

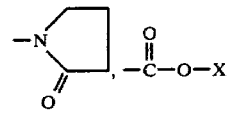

wherein X represents dimethylaminoethyl optionally quaternized and $C_{18}H_{37}$,

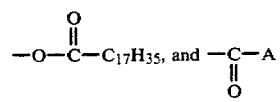

wherein A is D-glucosamine radical.

According to this embodiment of the invention, the anti-solar polymers have a content of the units of formula II generally between 15 and 100%, and preferably between 20 and 80%, by weight, relative to the total weight of the polymer.

The amount of the comonomer present in the anti-solar polymer of formula III of the present invention is variable but it is generally between about 20 and 90% of the total weight of the polymer, and preferably between 20 and 85%.

This latter content, as can be seen, cay vary rather widely and the particular content selected can depend, for instance, on the particular use chosen for the resulting polymer.

Also, the anti-solar polymers of formula II are characterized in that the weight of the repeating unit is between about 10–100%, generally between 15–100%, of the total weight of the polymer, and preferably between 20 and 80%.

The present invention also relates to a process for preparing the said anti-solar polymers.

In one embodiment, this process comprises preparing in a first stage a monomer, designated a "solar-filter monomer", of the formula

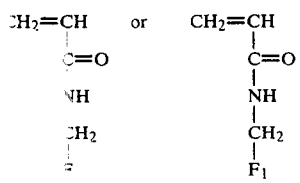

wherein F and $F_1$ have the same meaning given above, this said monomer in a second stage then being homopolymerized or copolymerized with one or more other comonomers.

The "solar-filter monomer" is prepared in a conventional manner by reacting, cold, in a sulfuric acid medium N-methylol acrylamide on the compound F or $F_1$. The time of the reaction is generally in the order of 10 hours to 4 days and is effected ordinarily at about ambient temperature.

The polymerization reaction can be effected according to conventional polymerization reactions, i.e., in mass, in solution, in suspension or in emulsion.

The polymerization initiators utilized are generally conventional free radical polymerization initiators and the choice of any one particular initiator can depend principally on the different monomers used as well as on the nature of reaction medium selected.

Representative usable initiators include the peroxides, such as benzoyl peroxide, lauroyl peroxide, acetyl peroxide, tertiobutyl hydroperoxide or benzoyl hydroperoxide, a catalyst which by decomposition liberates an inert gas, such as azobisisobutyonitrile, an oxidation-reduction catalyst such as sodium persulfate, sodium sulfite and $H_2O_2$. The concentration of the initiator is generally between about 0.2–35 weight percent, preferably between 0.5–20 weight percent, of the total weight of the monomer content.

The molecular weight of the anti-solar polymers of the present invention can be regulated by introducing, during the course of polymerization reaction, small amounts, i.e. about 0.05–0.15 weight percent of a chain regulating agent such as an aldehyde, for instance, butyraldehyde or a halogenated substance such as chloroform, bromoform, carbon tetrachloride, and the like.

At the end of the polymerization reaction, the polymer obtained can, if desired, be purified by, for example, treating it with an ion exchange resin.

The present invention also relates to an anti-solar cosmetic composition containing as the active component for absorbing wave length of light in the range of 280 to 315 millimicrons at least one anti-solar polymer as described above.

These cosmetic compositions can be present in diverse forms, the choice of any particular form being dependent upon the desired use of the composition. Preferably, these compositions are present in the form of an aqueous emulsion, lotion, cream, milk, gel or in the form of an aerosol. These compositions can also be present in the form of an aqueous or hydroalcoholic (ethanol or isopropanol) solution or even in the form of an oily solution.

When the compositions of the present invention are present in the form of an aerosol, they are packaged under pressure in a conventional aerosol bomb or container in the presence of a propellant gas which is preferably a halogenated hydrocarbon or a mixture of said hydrocarbons, such as, for example, mixtures of trichlorofluoromethane and dichlorodifluoromethane.

In these cosmetic compositions, the concentration of the polymers described above can be varied for any particular concentration can depend on the degree of protection desired. However, the concentration of the anti-solar polymer in these compositions is generally between about 0.2–20% by weight of the total composition.

These anti-solar cosmetic compositions can also contain conventional cosmetic adjuvants such as fatty bodies (oils, fats and waxes), emulsifying agents, surfactants, perfumes, silicone oils, pigments, dyes or preservatives.

The incorporation into these compositions of colored pigments also permits coloring the skin and masking skin flaws.

By applying to the skin the composition of the present invention, there is formed a film exhibiting good affinity vis-a-vis the epidermis, thus assuring excellent protection against wave lengths of eight in the erythematous zone.

The present anti-solar polymers have been found to be non-toxic and their excellent protective action is 2–3 times greater than achieved by the same F or $F_1$ compound but which is not fixed to a polymer.

In addition to this protective action of the skin vis-a-vis solar rays, the polymers of the present invention can also be used to protect, against degradation, dyes contained in various cosmetic formulations such as for example a hair dye composition, a hair tinting composition and the like.

In the examples which follow, the absorbing strength of the "solar-filter monomer" has been defined by means of its $K_{sp}$, which is a function of the quantity of filtering substance contained in the sample, of the optical density measured and of a constant depending on the particular apparatus used to measure the optical density.

The definition of the $K_{sp}$ which is given in "Introduction to Electronic Absorption Spectroscopy in Organic Chemistry", by Gillam and Stern, Arnold Ed. London, 1954, page 10, is:

$$K \text{ specific} = K_{sp} = K/c$$

where $K = d/l$ and $c =$ concentration of the solution in g/ml, $d =$ measured optical density and $l =$ thickness of the cell of the apparatus, expressed in cm.

The following examples are given to illustrate the present invention. Unless otherwise specified, all parts and percentages are by weight.

EXAMPLE 1

Preparation of acrylamido methyl-4-hydroxy-benzo phenone of the formula

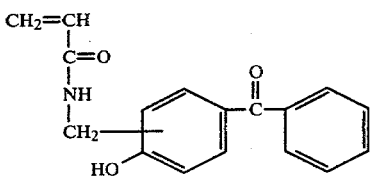

Into a 500 ml flask provided with a condenser, a nitrogen lead in tube and an agitator, and containing 19.8 g of benzophenone in solution in 70 g of sulfuric acid, there are introduced, in portions, 10 grams of N-methylol acrylamide while cooling the same.

The resulting mixture is thoroughly admixed by vigorously stirring the same and a light yellow solid forms. Agitation of the mixture is continued for 36 hours, then the solution is left to stand at rest for 48 hours at ambient temperature.

The mixture is then precipitated in a mixture of water and ice; the resulting precipitate being filtered, washed and taken up in ether.

The organic layers are washed with water until neutrality is reached. The ether phase is then dried with the ether being evaporated and the residue then dried under reduced pressure.

After two recrystallization in acetone, 20 grams of pure product are obtained.

Melting point = 159° C.

$\lambda_{max_1}{}^{EtOH} = 236$ millimicrons, $K_{sp} = 62,000$.

$\lambda_{max_2}{}^{EtOH} = 296$ millimicrons, $K_{sp} = 50,000$.

EXAMPLE 2

Preparation of a copolymer of acrylamido methyl-4-hydroxy benzophenone/stearyl methacrylate.

Into a 50 ml flask provided with a condenser, a nitrogen lead in tube and an agitator, there are intorduced 1 g of acrylamido methyl 4-hydroxy benzophenone, 1.5 g of stearyl methacrylate and 0.25 g of azobis-isobutyronitrile in solution in 5 ml of acetone. The resulting mixture is heated for 8 hours at 80° C.

The mixture is then diluted with acetone and the polymer is precipitated in methanol, yielding 1.6 g of pure polymer.

$\lambda_{max}{}^{Hexane} = 295$ millimicrons, $K_{sp} = 12,900$.

EXAMPLE 3

The preparation of acrylamido methyl-4-methoxy-2-hydroxy benzophenone of the formula

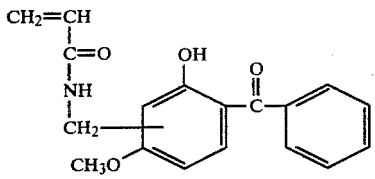

Into a 250 ml flask provided with a condenser, a nitrogen lead in tube and an agitator, and containing 22.8 g of 4-methoxy-2-hydroxy benzophenone in solution in 60 g of sulfuric acid cooled by ice. There are introduced, in portions, 10 g of N-methylol acrylamide. The resulting solution is left to stand, with agitation, for 24 hours, after which it is left to stand, at rest, for 2 days at ambient temperature.

The mixture is then poured over ice thereby producing a light brown precipitate which is filtered, washed with water and ethyl acetate. After drying, the resulting product is recrystallized in isopropanol.

Melting Point = 194° C.

$\lambda_{max}{}^{CHCl_3} = 293$ millimicrons, $K_{sp} = 52,200$.

EXAMPLE 4

Preparation of a copolymer of acrylamido methyl-4-methoxy-2-hydroxy benzophenone/stearyl methacrylate.

Into a 50 ml flask provided with a condenser, a nitrogen lead in tube and an agitator, there are introduced 2.5 g of acrylamido methyl-4-methoxy-2-hydroxy benzophenone, 2.5 g of stearyl methacrylate and 0.2 g of azobis-isobutyronitrile in solution in 10 g of acetone.

The resulting mixture is heated for 8 hours at 80° C., then diluted with benzene and finally precipitated in methanol, yielding 1.9 g of pure polymer.

$\lambda_{max}{}^{EtOH} = 287$ millimicrons, $K_{sp} = 10,600$.

EXAMPLE 5

Preparation of 3-(acrylamido methyl benzylidene) DL camphor of the formula

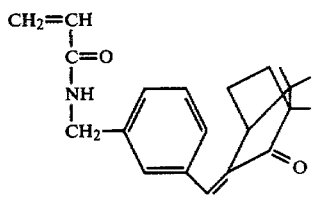

Into a one liter reactor provided with a mechanical agitator, a condenser and a calcium chloride guard, there are dissolved 120 g of a benzylidene DL camphor in 240 g of pure sulfuric acid.

Thereafter, there is introduced into the resulting solution 1 g of sodium nitrite and the mixture is cooled with an ice bath.

When the interior temperature reaches 0° C. there are then introduced over a one hour period 56 g of N-methylol acrylamide. The resulting mixture is left to stand at ambient temperature while being stirred for 48 hours.

The resulting thick brown solution is then slowly poured into a mixture of 500 g of ice and 500 g of water with vigorous agitation.

A light beige precipitate forms which is recovered and washed with water and then put into solution in 500 ml of ethyl acetate.

The organic layers are washed with water until the wash waters are neutral at which time they are dried on anhydrous sodium sulfate.

After filtering and evaporation of the solvent, the product is dried under reduced pressure, thus yielding 60 g of an oil which crystallizes on cooling. The crude product is then washed with 90 ml of sulfuric ether and the solid residue is then filtered and dried, yielding 31 g which are recrystallize in carbon tetrachloride (28 g).

Melting point = 134° C.

$\lambda_{max}{}^{CHCl_3} = 295$ millimicrons, $K_{sp} = 80,000$.

EXAMPLE 6

Preparation of a homopolymer of 3-(acrylamido methyl benzylidene) D.L. camphor.

Into a 25 ml flask provided with a condenser, a nitrogen lead in tube and an agitator, there are introduced 4 g of crude 3-(acrylamido methyl benzylidene) D.L. camphor, obtained in the manner set forth in Example 5, and 0.4 g of azobis-isobutyronitrile dissolved in 4 ml of methanol. The resulting mixture is heated for 24 hours at the reflux of methanol and, after cooling, the precipitated polymer is dissolved in chloroform.

This solution is then poured into methanol and the precipitated polymer is filtered and dried under reduced pressure, yielding 2.5 g of pure product.

$\lambda_{max}^{CHCl} = 296$ millimicrons, $K_{sp} = 52,000$.

EXAMPLE 7

Preparation of a copolymer of 3-(acrylamido methyl benzylidene) D.L. camphor/stearyl methacrylate.

Into a 100 ml flask, provided with a condenser, a nitrogen lead in tube and an agitator, there are introduced 15 g of pure 3-(acrylamido methyl benzylidene) D.L. camphor, 15 g of stearyl methacrylate, 3 g of azobis-isobutyronitrile and 60 g of acetone. The resulting solution is heated, with agitation, for 24 hours at 80° C. and the polymer precipitates on cooling. After filtering the polymer therefrom, it is dissolved in heptane and precipitated in 2 liters of absolute ethanol, yielding 15 g of pure product.

$\lambda_{max}^{Heptane} = 291$ millimicrons, $K_{sp} = 20,000$.

EXAMPLE 8

Preparation of a copolymer of 3-(acrylamido methyl benzylidene) D.L. camphor/dimethylamino ethyl methacrylate quaternized with dimethyl sulfate.

Into a 250 ml flask provided with a condenser, a nitrogen lead in tube and an agitator, there are introduced 15 g of 3-(acrylamido methyl benzylidene) D.L. camphor, 5 g of dimethylaminoethyl methacrylate, 2 g of azobis-isobutyronitride and 40 g of dioxane.

The resulting solution is agitated for 24 hours at 80° C. after which there are introduced 5 g of dimethyl sulfate in solution in 20 g of methanol.

The temperature of the resulting mixture is held for 4 hours at 80° C. at which time the polymer is precipitated in 2 liters of ethyl acetate, yielding 17 g of pure polymer.

$\lambda_{max}^{EtOH+H2O} = 295$ millimicrons, $K_{sp} = 25,500$.

EXAMPLE 9

Preparation of a copolymer of 3-(acrylamido methyl benzylidene) D.L. camphor/methylmethacrylate/-dimethylaminoethyl methacrylate quaternized with dimethyl sulfate.

Into a 100 ml flask provided with a condenser, a nitrogen lead in tube and an agitator, there are introduced 8 g of 3-(acrylamido methyl benzylidene) D.L. camphor, 8 g of methyl methacrylate, 8 g of dimethylaminoethyl methacrylate, 0.24 g of azobis-isobutyronitrile and 24 g of absolute ethanol.

The resulting solution is held at a temperature of 80° C. for 10 hours with agitation at which time there are introduced 5 g of dimethyl sulfate in solution in 25 ml of methanol. The temperature of the solution is held for four additional hours at 80° C. Thereafter, the polymer is precipitated in ethyl acetate, yielding 22 g of pure product.

$\lambda_{max}^{EtOH+H2O} = 295$ millimicrons, $K_{sp} = 8,500$.

EXAMPLE 10

Preparation of a copolymer of 3-(acrylamido methyl benzylidene) D.L. camphor/N-vinyl pyrrolidone.

Into a 25 ml flask provided with a condenser, a nitrogen lead in tube and an agitator, there are introduced 0.5 g of 3-(acrylamido methyl benzylidene) D.L. camphor, 2 g of N-vinylpyrrolidone, 0.15 g of azobis-isobutyronitrile and 3 g of ethanol.

The resulting mixture is heated for 8 hours at 80° C. and the polymer is precipitated in an 8:1 mixture of sulfuric ether and isopropanol, yielding 1.5 g of pure polymer.

$\lambda_{max}^{EtOH+H2O} = 298$ millimicrons, $K_{sp} = 18,100$.

EXAMPLE 11

Preparation of a copolymer of 3-(acrylamido methyl benzylidene) D.L. camphor/methylacrylate/dimethylaminoethyl methacrylate quaternized with dimethyl sulfate.

Into a 250 ml flask provided with an agitator, a condenser and a nitrogen lead in tube, there are introduced 12 g of 3-(acrylamido methyl benzylidene) D.L. camphor, 8 g of dimethylaminoethyl methacrylate, 8 g of methyl acrylate, 0.3 g of azobis-isobutyronitrile and 28 g of absolute ethanol.

The resulting solution is heated for 8 hours at 80° C. and, after cooling, there are introduced 7 g of dimethyl sulfate in solution in 28 g of methanol. The resulting solution is heated for 24 hours at 80° C.

The polymer is precipitated in a 50:50 mixture of ethylacetate and dioxane, yielding 24 g of pure polymer.

$\lambda_{max}^{EtOH+H2O} = 295$ millimicrons, $K_{sp} = 17,800$.

EXAMPLE 12

Preparation of a copolymer of 3-(acrylamido methyl benzylidene) D.L. camphor/N-methacryloyl D-glucosamine.

In a 50 ml flask provided with a condenser, a nitrogen lead in tube and an agitator, there are dissolved 5 g of N-methacryloyl D glucosamine, 5 g of 3-(acrylamido methyl benzylidene) D.L. camphor and 0.5 g of azobis-isobutyronitrile in 30 g of dimethylformamide.

The resulting solution is heated for 24 hours at 80° C. The polymer is then precipitated in water, cooled in a 50:50 mixture of ethanol and methanol and precipitated in an 8:1 mixture of sulfuric ether and isopropanol, yielding 6 g of pure polymer $\lambda_{max}^{EtOH+H2O} = 297$ millimicrons, $K_{sp} = 24,200$.

EXAMPLE 13

Preparation of a copolymer of 3-(acrylamido methyl benzylidene) D.L. camphor/stearyl acrylate.

Into a 10 ml flask provided with a condenser, a nitrogen lead in tube and an agitator, there are introduced 1.6 g of 3-(acrylamido methyl benzylidene) D.L. camphor, 0.6 g of stearyl acrylate and 0.2 g of azobis-isobutyronitrile in solution in 3 g of acetone.

The resulting solution is heated to reflux for 18 hours at which time the polymer is precipitated in 250 ml of methanol, yielding 018 g of pure polymer.

$\lambda_{max}^{CHCl3} = 295$ millimicrons, $K_{sp} = 51,100$.

EXAMPLE 14

Preparation of a copolymer of 3-(acrylamido methyl benzylidene) D.L. camphor/stearyl methacrylate/-methyl acrylate.

Into a 10 ml flask provided with a condenser, a nitrogen lead in tube and an agitator, there are introduced 1.2 g of 3-(acrylamido methyl benzylidene) D.L. camphor, 0.6 g of stearyl methacrylate, 0.2 g of methyl acrylate and 0.2 g of azobis-isobutyronitrile in 3 g of acetone.

The resulting solution is held at a temperature of 80° C. for 18 hours at which time it is diluted with 10 ml of heptane and poured into 500 ml of methanol to precipitate the polymer, yielding 1.3 g of the pure polymer.

$\lambda_{max}^{CHCl_3} = 295$ millimicrons, $K_{sp} = 36,500$.

EXAMPLE 15

Preparation of acrylamido methyl-7-hydroxy-4-methyl coumarin of the formula

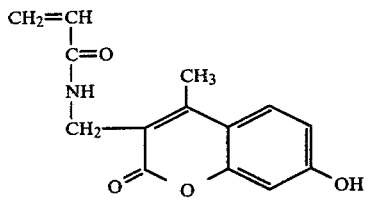

Into a 250 ml flask provided with a condenser, a nitrogen lead in tube and an agitator, and containing 17.6 g of 7-hydroxy-4-methyl coumarin and 60 g of pure sulfuric acid cooled in ice, there are introduced 10 g of N-methylol acrylamide.

The resulting mixture is agitated for 2 days at ambient temperature and then left to stand at rest for an additional 2 days.

The solution is then poured into ice and the resulting precipitate is taken up in ethylacetate, washed with water and dried under reduced pressure. After recrystallizing the precipitate in ethanol there are obtained 10 g of pure product.

$\lambda_{max}^{CHCl_3} = 323$ millimicrons.

EXAMPLE 16

Preparation of a copolymer of acrylamido methyl-7-hydroxy-4-methyl coumarin/stearyl methacrylate.

Into a 50 ml flask provided with a condenser, a nitrogen lead in tube and an agitator, there are introduced 1 g of acrylamido methyl 7-hydroxy-4-methyl coumarin, 2 g of stearyl methacrylate, 0.3 g of azobis-isobutyronitrile and 6 g of dimethylformamide.

The resulting mixture is heated for 8 hours at 80° C. at which time it is diluted with benzene and the polymer is then precipitated in methanol, yielding 1.2 g of pure polymer.

$\lambda_{max}^{Hexane} = 324$ millimicrons, $K_{sp} = 6,300$.

EXAMPLE 17

Preparation of 3-(acrylamidomethyl)4-hydroxy coumarin of the formula

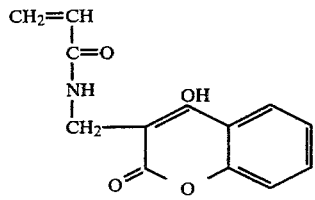

In a 250 ml flask provided with a condenser, a nitrogen lead in tube and an agitator, there are dissolved 16.2 g of 4-hydroxy coumarin in 50 g of pure sulfuric acid. The reaction is exothermic and the temperature reaches 80° C. After cooling to 0° C. by a mixture of ice and salt, 11 g of N-methylol acrylamide are slowly added thereto.

The resulting mixture is then left to stand with agitation until its temperature returns to ambient temperature. Agitation of the same is then continued for an additional 4 days, at which time the solution is poured into a mixture of ice and water to precipitate the polymer in the form of a beige powder which is filtered, washed with water, dried under reduced pressure and recrystallized in ethanol, yielding 15 g of the polymer, having a melting point of 194° C.

$\lambda_{max}^{EtOH+H2O} = 288$ millimicrons, $K_{sp} = 48,00$.
$\lambda_{max}^{EtOH+H2O} = 304$ millimicrons, $K_{sp} = 50,000$.

EXAMPLE 18

Preparation of a homopolymer of 3-(acrylamido methyl)-4-hydroxy coumarin.

Into a 50 ml flask provided with a condenser, a nitrogen lead in tube and an agitator, there are introduced 2.5 g of 3-(acrylamido methyl)-4-hydroxy coumarin and 0.25 g of azobis-isobutyronitrile in 15 ml of dimethylformamide.

The resulting mixture is heated for 24 hours at 100° C. at which time the homopolymer is precipitated in lukewarm dichloromethane, yielding 0.6 g of product.

$\lambda_{max}^{MeOCH2CH2OH} = 310$ millimicrons, $K_{sp} = 14,200$.

EXAMPLE 19

Preparation of a copolymer of 3-(acrylamido methyl)-4-hydroxy coumarin/N-vinyl pyrrolidone.

Into a 50 ml flask provided with a condenser, a nitrogen lead in tube and an agitator, there are introduced 3 g of 3-(acrylamido methyl)-4-hydroxy coumarin, 7 g of N-vinyl pyrrolidone, 0.5 g of azobis-isobutyronitrile and 10 g of dimethylformamide.

The resulting solution is agitated for 24 hours at 100° C. at which time it is poured into sulfuric ether thereby precipitating the polymer.

The solution is filtered and this recovered precipitate is dissolved in methanol and cooled in nitromethane, thus yielding 3 g of pure polymer.

$\lambda_{max}^{EtOH} = 282$ millimicrons, $K_{sp} = 4,540$.
$\lambda_{max}^{EtOH} = 305$ millimicrons, $K_{sp} = 4,200$.

EXAMPLE 20

Preparation of a copolymer of 3-(acrylamido methyl)-4-hydroxy coumarin/dimethylaminoethyl methacrylate quaternized with dimethyl sulfate.

Into a 50 ml flask provided with a condenser, a nitrogen lead in tube and an agitator, there are introduced 7 g of 3-(acrylamido methyl)-4-hydroxy coumarin, 3 g of dimethylaminoethyl methacrylate quaternized with dimethyl sulfate, 1 g of azobis-isobutyronitrile and 30 g of dimethylformamide.

The resulting mixture is heated for 24 hours at 100° C. at which time it is poured into lukewarm dichloromethane to precipitate the polymer which is then filtered therefrom and dried, yielding 5 g of pure polymer.

$\lambda_{max1}^{H2O} = 302$ millimicrons, $K_{sp} = 12,200$.
$\lambda_{max}^{H2O} = 290$ millimicrons, $K_{sp} = 11,900$.

EXAMPLE 21

Preparation of a copolymer of stearylacrylate/3-(acrylamido methyl)-4-hydroxy coumarin/acrylamido methyl-4-hydroxy benzophenone/3-(acrylamido methyl benzylidene) D.L. camphor.

Into a 50 ml flask provided with a condenser, a nitrogen lead in tube and an agitator, there are introduced 2 g of 3-(acrylamido methyl)-4-hydroxy coumarin, 1 g of acrylamido methyl-4-hydroxy benzophenone, 0.5 g of 3-(acrylamido methyl benzylidene) D.L. camphor, 3.5 g of stearylacrylate, 0.7 g of azobis-isobutyronitrile and 15 g of dimethylformamide.

The resulting mixture is heated, with agitation, at 80° C. for 24 hours at which time it is diluted with chloroform, filtered and then precipitated in 800 ml of lukewarm acetone.

The resulting polymer which precipitates is filtered therefrom, washed and dried under a reduced pressure, yielding 4.1 g of pure polymer.

$\lambda_{max_1}{}^{CHCl_3} = 284$ millimicrons, $K_{sp} = 20,000$.
$\lambda_{max_2}{}^{CH_3Cl_3} = 298$ millimicrons, $K_{sp} = 17,500$.

EXAMPLE 22

Preparation of 2-[(acrylamido-methyl-2'-hydroxy-5'-methyl)phenyl]-2H-benzotriazole having the formula

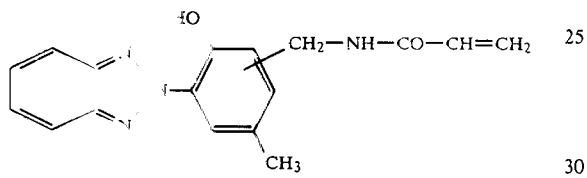

192 g of pure sulfuric acid and 72 g of 2-[(2'-hydroxy-5'-methyl)phenyl]-2H-benzotriazole are introduced under nitrogen gas into a round bottom flask. The resulting mixture is cooled to 0° C. and 31.5 g of N-hydroxymethyl acrylamide are added thereto. The temperature of the reaction mixture is permitted to return to ambient temperature and the reaction mixture is agitated for 18 hours. Thereafter the reaction mixture is poured into water and then filtered. After recrystallization in chloroform 55 g of pure product are obtained.

Yield: 56%.
Melting Point: 204° C.
$\lambda_{max_1}{}^{THF} = 302$ millimicrons, $K_{sp} = 55,000$.
$\lambda_{max_2}{}^{THF} = 339$ millimicrons, $K_{sp} = 57,000$.

In a similar fashion, acrylamidomethyl 2-phenylbenzimidazole is prepared.

EXAMPLE 23

Preparation of a copolymer of 2-[(acrylamidomethyl-2'-hydroxy-5'-methyl)phenyl]-2H-benzotriazole/2-N,N-dimethylamino ethyl methacrylate quaternized with dimethyl sulfate.

2 g of the anti-solar monomer prepared in Example 22, 8 g of 2-N,N-dimethylamino ethyl methacrylate quaternized with dimethyl sulfate, 20 g of DMF and 1 g of azobis-isobutyronitrile are introduced under nitrogen gas into a round bottom flask. The resulting mixture is heated to 80° C. for 24 hours and then left to cool. The thus cooled mixture is diluted with 20 ml of methanol and poured slowly into 500 ml of acetone. The above resulting copolymer is filtered and dried under reduced pressure, thus providing 8 g of the copolymer which is soluble in water.

Yield = 80%.
$\lambda_{max_1}{}^{DMF} = 298$ millimicrons, $K_{sp} = 6,200$.
$\lambda_{max_2}{}^{DMF} = 335$ millimicrons, $K_{sp} = 5,200$.
DMF means dimethylformamide.

In a similar fashion, a copolymer of acrylamidoethyl-2-phenyl benzimidazole/2-N,N-dimethylamino ethyl methacrylate quaternized with dimethyl sulfate is prepared.

EXAMPLE 24

Preparation of a copolymer of 2-[(acrylamidomethyl-2'-hydroxy-5'-methyl)phenyl]-2H-benzotriazole/stearyl acrylate.

50 g of the solar-filter monomer prepared according to Example 22, 33.4 g of stearyl acrylate, 150 g of THF and 5 g of azobis-isobutyronitrile are introduced into a round bottom flask. The resulting mixture is heated at 80° C. for 9 hours after which it is poured into 7 liters of methanol. After filtering and drying under reduced pressure 70 g of the above copolymer which is soluble in oil are obtained.

Yield = 85%.
$\lambda_{max_1}{}^{THF} = 303$ millimicrons, $K_{sp} = 28,300$.
$\lambda_{max_2}{}^{THF} = 339$ millimicrons, $K_{sp} = 28,000$.
THF means tetrahydrofuran.

In a similar manner a copolymer of acrylamido methyl-2-phenyl benzimidazole/stearyl acrylate is prepared.

EXAMPLE 25

Preparation of a copolymer of 3-(acrylamido methyl benzylidene) D.L. camphor/stearyl acrylate/methyl acrylate.

Into a 10 ml flask provided with a condenser, a nitrogen lead in tube and an agitator, there are introduced 1.2 g of 3-acrylamido methyl benzylidene) D.L. camphor, 0.6 g of stearyl acrylate, 0.2 g of methyl acrylate and 0.2 g of azobisisobutyronitrile in 3 g of acetone.

The resulting solution is held at reflux temperature for 18 hours at which time it is diluted with 10 ml of heptane and poured into 500 ml of methanol to precipitate the polymer, yielding 0.8 g of the pure polymer.
$\lambda_{max}{}^{CHCl_3} = 294$ millimicrons, $K_{sp} = 32,700$.

EXAMPLES OF COSMETIC COMPOSITIONS

EXAMPLES 26-30

An anti-solar oil composition in accordance with the present invention is prepared by admixing the following components:

Polymer of Example 2: 10 g
Perfume: 0.5 g
Hydroxybutyltoluene: 0.0625 g
Vaseline oil, q.s.p.: 100 g The above anti-solar oil composition is repeated except that the polymer of Example 2 is replaced by the same quantity of the polymer prepared in accordance with each of Examples 4, 7 16 and 21. A comparably effective anti-solar oil composition results in each instance.

EXAMPLES 31-34

An anti-solar lotion in accordance with the present invention is prepared by admixing the following components:

Polymer of Example 13: 5 g
Lanolin: 2.5 g
Hydroxybutylanisole (antioxidant): 0.0625
Triglycerides of octanoic and decanoic acids: 40 g
Ethyl alcohol (96%).q.s.p.: 100 g The above anti-solar lotion is repeated except that the polymer of Example 13 is replaced by the same quantity of the polymer prepared in accordance with each of Examples 14, 15 and 21. A comparably effective anti-solar lotion results in each instance.

EXAMPLES 35–36

An anti-solar aerosol composition in accordance with the present invention is prepared by admixing the following components:
Polymer of Example 13: 5 g
Absolute ethyl alcohol: 30 g
Isopropyl palmitate: 20 g
Ricin oil: 2 g
Lanolin: 2 g
Perfume: 1 g
Dichlorodifluoromethane (propellant): 40 g The above aerosol composition is packaged under pressure in a conventional aerosol container.

Further, the above aerosol composition is repeated except that the polymer of Example 13 is replaced by the same quantity of the polymer prepared in accordance with Example 21. A comparably effective anti-solar aerosol formulation results.

EXAMPLES 37–39

An anti-solar aerosol foam composition in accordance with the present invention is prepared by admixing the following components:
Polymer of Example 4: 10 g
Stearic acid: 0.5 g
Lauric acid: 0.5 g
Palmitic acid: 2.5 g
Vaseline oil: 45.7 g
Ethyl p-hydroxybenzoate: 0.3 g
Triethanolamine: 1.5 g
Reliculated polyacrylic acid sold under the tradename CARBOPOL (0.05% solution in $H_2O$)-carboxy-polymethylene: 38.5 g
Perfume: 0.5 g 85 g of the above composition are packaged under pressure in a conventional aerosol container or bomb together with 13 g of dichlorodifluoromethane.

The above aerosol formulation is repeated except that the polymer of Example 4 is replaced by the same quantity of the polymer prepared in accordance with each of Examples 7 and 16. A comparably effective anti-solar aerosol foam results in each instance.

EXAMPLE 40–41

An anti-solar cream is prepared in accordance with the present invention by admixing the following components:
Polymer of Example 15: 10 g
Triglycerides of octanoic and decanoic acids: 31 g
Glycerol monostearate: 6 g
Polyethylene glycol stearate: 2 g
Stearic acid: 2 g
Cetyl alcohol: 1.2 g
Lanolin: 4 g
Silicone oil: 1 g
Methyl p-hydroxybenzoate: 0.3 g
Propylene glycol: 2 g
Triethanolamine: 0.1 g
Perfume: 0.5 g
Water,q.s.p.: 100 g The above anti-solar cream formulation is repeated except that the polymer of Example 15 is replaced by the same quantity of the polymer prepared in accordance with Example 14. A comparably effective anti-solar cream results.

EXAMPLE 42

An anti-solar milk is prepared in accordance with the present invention by admixing the following components:
Polymer of Example 2: 5 g
Cetyl-stearyl alcohol: 2 g
Cetyl alcohol: 2 g
Vaseline oil: 20 g
Lanolin: 4 g
Stearic acid: 0.5 g
Silicone oil: 0.3 g
Propyl p-hydroxy benzoate: 0.4 g
Glycerin: 5 g
Reliculated polyacrylic acid sold under the tradename CARBOPOL (carboxypolymethylene): 0.15 g
Triethanolamine: 0.20 g
Perfume: 0.3 g
Water,q.s.p.: 100 g

EXAMPLES 43–47

An anti-solar cream formulation in accordance with the present invention is prepared by admixing the following components:
Polymer of Example 8: 15 g
Cetyl-stearyl alcohol: 2 g
Glycerol monostearate: 4 g
Cetyl alcohol: 4 g
Vaseline oil: 5 g
Butyl stearate: 5 g
Propylene glycol: 7 g
Silicone oil: 0.125 g
Nonionic polymer of high molecular weight sold under the tradename POLYOX (5% solution in water): 3.5 g
Methyl-p-hyroxy benzoate: 0.3 g
Perfume: 0.4 g
Water, q.s.p.: 100 g The above anti-solar cream formulation is repeated except that the polymer of Example 8 is replaced by the same quantity of the polymer prepared in accordance with Examples 9, 10, 11 and 12. A comparably effective anti-solar cream results in each instance.

EXAMPLE 48

An anti-solar milk in accordance with the present invention is prepared by admixing the following components:
Polymer of Example 19: 5 g
Polymer of Example 20: 5 g
Sipol wax: 5 g
Vaseline oil: 6 g
Isopropyl myristate: 3 g
Propyl p-hydroxy benzoate: 0.3 g
Glycerin: 20 g
Perfume: 0.3 g
Water, q.s.p.: 100 g

EXAMPLE 49

An anti-solar aerosol foam composition in accordance with the present invention is prepared by admixing the following components:
Polymer of Example 10: 10 g
Sipol wax: 3.5 g
Vaseline oil: 6 g
Isopropyl myristate: 3 g
Methyl-p-hydroxybenzoate: 0.3 g Glycerin: 10 g
Perfume: 0.3 g
Water, q.s.p.: 100 g 37 g of the above composition are packaged in a conventional aerosol container together with 13 g of dichlorodiflouromethane.

EXAMPLES 50–51

An anti-solar aerosol formulation in accordance with the present invention is prepared by admixing the following components.

Polymer of Example 6: 5 g
Methylcellosolve: 30 g
Isopropyl myristate: 20 g
Ricin oil: 2 g
Lanolin: 2 g
Perfume: 1 g
Dichlorodifluoromethane (Propellant): 40 g The above aerosol formulation is packaged under pressure in a conventional aerosol container.

Further, the above aerosol aerosol formulation is repeated except that the polymer of Example 6 is replaced by the same quantity of the polymer prepared in accordance with Example 18. A comparably effective anti-solar aerosol formulation results.

USE OF ANTI-SOLAR COPOLYMERS TO PROTECT DYES

EXAMPLE 52

A hair-setting lotion for coloring hair is prepared in accordance with the present invention by admixing the following components:

Copolymer of Example 11: 0.3 g
Copolymer of vinylpyrrolidone/vinyl acetate, 70/30, M.W.=40,000: 2 g
Ethyl alcohol: 50 g
Dye-CI Basic Violet 1 (CI 42535): 0.002 g
Water, q.s.p.: 100 g

EXAMPLE 53

A hair setting lotion for coloring hair is prepared in accordance with the present invention by admixing the following components:

Copolymer of Example 12: 0.3 g
Copolymer of crotonic acid/vinyl acetate, 90/10, MW=40,000: 2 g
Ethyl alcohol: 50 g
Triethanolamine, q.s.p.: pH7
Dye-CI Basic Violet 3 (CI 42555): 0.002 g
Dye-Basic Violet 1 (CI 42535): 0.001 g
Water, q.s.p.: 100 g

EXAMPLE 54

An anti-solar cream is prepared by admixing the following components:

Polymer of Example 23: 15 g
Cetyl stearyl alcohol: 2 g
Glycerol monostearate: 4 g
Cetyl alcohol: 4 g
Vaseline oil: 5 g
Butyl stearate: 5 g
Propylene glycol: 7 g
Silicone oil: 0.125 g
Non-ionic polymer, high molecular weight sold under the mark POLYOX in a 5% aqueous solution: 3.5 g
Methyl p-hydroxybenzoate: 0.3 g Perfume: 0.5 g
Water, q.s.p.: 100 g

EXAMPLE 55

An anti-solar oil is prepared by admixing the following components:

Polymer of Example 24: 10 g
Perfume: 0.4 g
Butylated hydroxytoluene: 0.0625 g
Colza oil, q.s.p.: 100 g

What is claimed is:

1. Anti-solar polymer having in the macromolecular chain from 10–100 percent by weight of units of the formula $$\left[\begin{array}{c} -CH_2-CH- \\ | \\ C=O \\ | \\ NH \\ | \\ CH_2 \\ | \\ F \end{array}\right]$$

wherein F is selected from the group consisting of

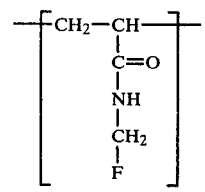
(1)

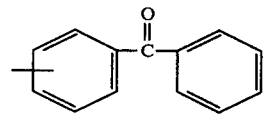
(2)

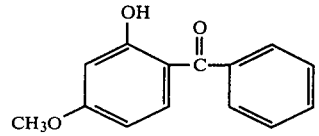
(3)

wherein R is selected from the group consisting of hydrogen and $CH_3$ and $R_1$ is selected from the group consisting of $CH_3$ and $OCH_3$

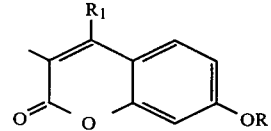
(4)

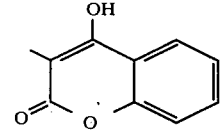
(5)

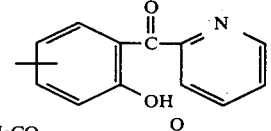
(6)

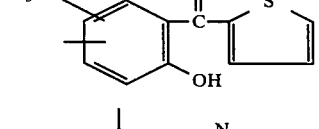

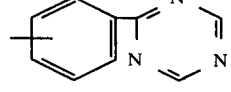
(7)

-continued (8) 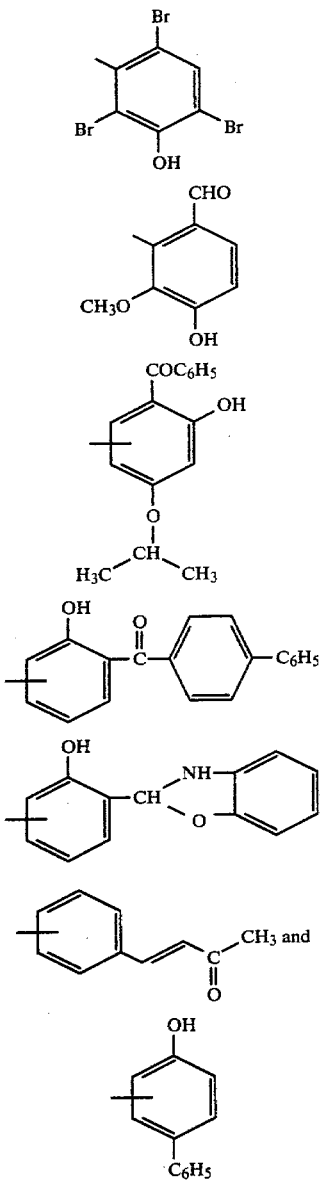

(9)

(10)

(11)

(12)

(13)

(14)

and from 90–0 percent by weight of units derived from an ethylenically unsaturated monomer, said polymer having an average molecular weight between about 2,000–1,000,000.

2. The polymer of claim 1 wherein said ethylenically unsaturated monomer is selected from the group consisting of (a) N-vinylpyrrolidone,
(b) N-methylacryloyl D-glucosamine
(c) dimethyl aminoethyl methacrylate,
(d) stearyl methacrylate,
(e) stearylacrylate, and
(f) vinyl stearate 3. The polymer of claim 1 having the formula

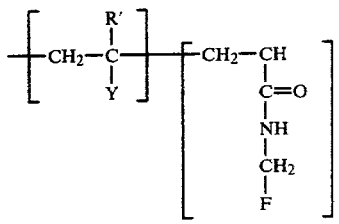

wherein F has the meaning given hereintofore, R' is selected from the group consisting of hydrogen and methyl and Y is selected from the group consisting of

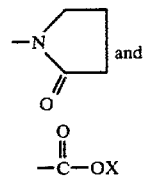 and  (i)

  (ii)

wherein X is selected from the group consisting of D-glucosamine, dimethylaminoethyl, quaternized dimethylaminoethyl and $C_{18}H_{37}$.

4. The polymer of claim 1 wherein the amount of ethylenically unsaturated monomer is about 20–90 percent of the total weight of the copolymer.

5. Anti-solar polymer having in the macromolecular chain thereof at least one unit of the formula

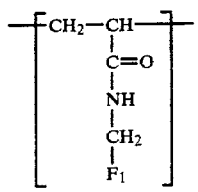

wherein $F_1$ is selected from the group consisting of

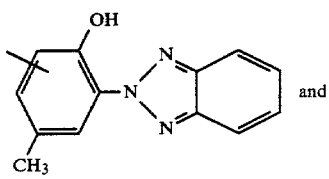 and

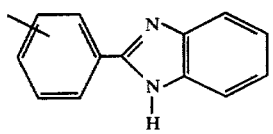

and from 90–0 percent by weight of units derived from an ethylenically unsaturated monomer, said polymer having an average molecular weight between about 2,000–1,000,000.

6. The polymer of claim 5 having the formula

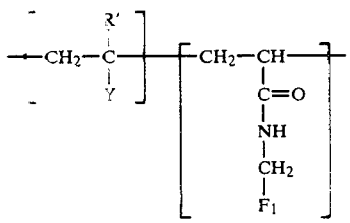

wherein $F_1$ has the meaning given in claim 5,

R' represents hydrogen or methyl and

Y represents a member selected from the group consisting of

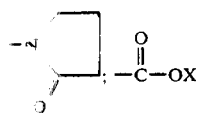

wherein X represents dimethylaminoethyl, quaternized dimethylaminoethyl and $C_{18}H_{37}$;

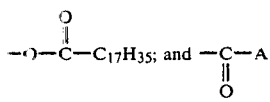

wherein A is D-glucosamine radical.

7. The polymer of claim 5 containing said absorbing unit in an amount between 15 and 100 weight percent based on the total weight of said polymer.

8. The polymer of claim 5 containing said absorbing unit in an amount between 20 and 80 weight percent based on the total weight of said polymer.

9. Anti-solar polymer selected from the group consisting of
(1) acrylamidomethyl-2-hydroxy-5 methyl benzotriazole/2-N,N-dimethylamino ethyl methacrylate quaternized with dimethyl sulfate,
(2) acrylamidomethyl-2-phenyl benzimidazole/2-N,N-dimethylaminoethyl methacrylate quaternized with dimethyl sulfate,
(3) acrylamidomethyl-2-hydroxy-5-methyl benzotriazole/stearyl acrylate; and
(4) acrylamidomethyl-2-phenyl benzimidazole/stearyl acrylate.

10. Anti-solar polymer having in the macromolecular chain thereof from 10–100 percent by weight of units of the formula

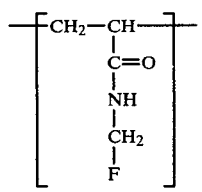

wherein F is a residue derived from an aromatic compound imparting to the said polymer the ability to absorb wavelengths of light in the range of about 280–315 millimicrons, and from 90–0 percent by weight of units derived from an ethylenically unsaturated monomer, said polymer having an average molecular weight between about 2,000–1,000,000.

11. The anti-solar polymer of claim 10 wherein said ethylenically unsaturated monomer is selected from the group consisting of
(a) N-vinylpyrrolidone,
(b) N-methylacryloyl D-glucosamine,
(c) dimethyl aminoethyl methacrylate,
(d) stearyl methacrylate,
(e) stearyl acrylate, and
(f) vinyl stearate.

* * * * *

UNITED STATES PATENT AND TRADEMARK OFFICE
CERTIFICATE OF CORRECTION

PATENT NO. : 4,233,430
DATED : November 11, 1980
INVENTOR(S) : Bernard Jacquet, et al It is certified that error appears in the above-identified patent and that said Letters Patent are hereby corrected as shown below:

Column 20, formula (2) at lines 34-38 should read:

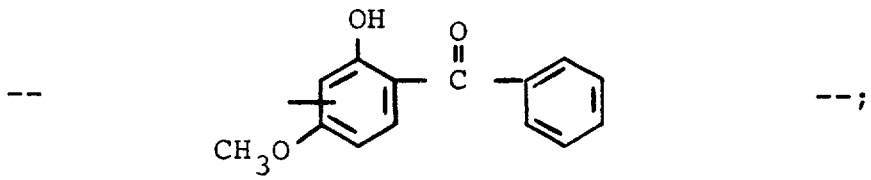

formula (7) at lines 64-68 should read:

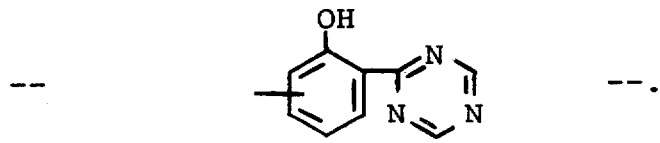

Signed and Sealed this

Sixth Day of October 1981

[SEAL]

Attest:

Attesting Officer

GERALD J. MOSSINGHOFF

Commissioner of Patents and Trademarks